(12) United States Patent
Alberati et al.

(10) Patent No.: US 8,153,679 B2
(45) Date of Patent: Apr. 10, 2012

(54) RADIOLABELLED INHIBITORS OF THE GLYCINE 1 TRANSPORTER

(75) Inventors: Daniela Alberati, Zofingen (CH); Edilio Maurizio Borroni, Basel (CH); Thomas Hartung, Loerrach (DE); Roger David Norcross, Olsberg (CH); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 349 days.

(21) Appl. No.: 12/607,111

(22) Filed: Oct. 28, 2009

(65) Prior Publication Data

US 2010/0111862 A1 May 6, 2010

(30) Foreign Application Priority Data

Nov. 4, 2008 (EP) .................................... 08168229

(51) Int. Cl.
*A61K 31/4035* (2006.01)
*C07D 209/44* (2006.01)
*C07D 405/04* (2006.01)
(52) U.S. Cl. ........ 514/414; 548/470; 548/482; 514/412; 424/1.65
(58) Field of Classification Search .................. 548/469, 548/470, 482; 514/412, 414; 424/1.65
See application file for complete search history.

(56) References Cited

U.S. PATENT DOCUMENTS 7,557,114 B2 * 7/2009 Jolidon et al. ............. 514/265.1

FOREIGN PATENT DOCUMENTS

| WO | WO 2005/014563 | 2/2005 |
| WO | WO 2006/082001 | 8/2006 |
| WO | WO 2007/041025 | 4/2007 |

OTHER PUBLICATIONS

Armer et al., Exp. Opin. Ther. Patents 11(4) pp. 563-572 (2001).
Pralong et al., Prog. Neurobiol. vol. 67, pp. 173-202 (2002).
Carlsson M. L., J. Neurol. Trans. 105 pp. 525-535 (1998).
Gee, British Medical Bulletin, vol. 65, pp. 169-177 (2003).
Larsen et al., J. Label Compounds Radiopharm. vol. 37, pp. 73-75 (1995).
Cubelos et al., Cereb. Cortex vol. 15 pp. 448-459 (2005).
Zafra et al., Neurosci. vol. 15 pp. 3952-3969 (1995).

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present invention relates to novel radiolabelled inhibitors of formula I for the Glycine 1 transporter (GlyT1), useful for the labelling and diagnostic imaging of the glycine 1 transporter functionality.

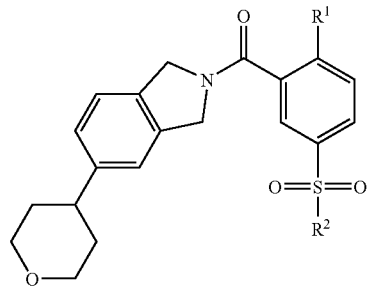

I wherein
$R^1$ is isopropoxy or 2,2,2-trifluoro-1-methyl-ethoxy; and
$R^2$ is a radiolabelled group $CH_3$, wherein the radionuclide is $^3H$ or $^{11}C$. The radiolabelled compounds of formula I may be used as PET (Positron Emission Tomography) radiotracer for the labelling and diagnostic molecular imaging of the glycine 1 transporter functionality.

10 Claims, No Drawings

RADIOLABELLED INHIBITORS OF THE GLYCINE 1 TRANSPORTER

PRIORITY TO RELATED APPLICATION(S)

This application claims the benefit of European Patent Application No. 08168229.6, field Nov. 4, 2008, which is hereby incorporated by reference in its entirety.

BACKGROUND OF THE INVENTION

Molecular imaging is based on the selective and specific interaction of a molecular probe (e.g. a radiotracer) with a biological target (for instance a receptor, an enzyme, an ion channel or any other cellular component that is able to bind or retain the molecular probe) which is visualized through PET, nuclear magnetic resonance, near infrared or other methods. PET, a nuclear medical imaging modality, is ideally suited to produce three-dimensional images that provide important information, on the distribution of a biological target in a given organ, or on the metabolic activity of such organ or cell or on the ability of a drug to enter such organ, bind to a biological target and/or modify biological processes. Since PET is a non-invasive imaging technique it can be used to investigate the pathophysiology of a disease and the action of drug on a given molecular target or cellular processes in humans and in animals. The availability of a PET radiotracer specific for a given molecular target can facilitate drug development and the understanding of the mechanism of action of a drug. In addition, a PET radiotracer may facilitate diagnosis of a disease by demonstrating pathophysiological changes taking place as a consequence of the disease.

Glycine transporter inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans*, 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563-572, 2001).

The human brain is a complex organ, consisting of millions of intercommunicating neurons. The understanding of abnormalities relating to diseases is the key to the future development of effective diagnosis and novel therapeutics. The study of biochemical abnormalities in humans is rapidly becoming an essential and integral component of drug discovery and development process. Traditionally, the discovery and development of new drugs has been performed with a heavy emphasis on in vitro techniques to select promising lead candidates which are subsequently tested in living animals prior to human administration. Because in vitro systems reflect only part of the complexity of living systems and in vivo animal models of human disease are often only an approximation of human pathology, there is growing realization that a robust understanding of drug-receptor interaction in living man at an early stage in this process will be a major driving force in further enhancing the efficient and timely discovery and development of novel therapeutics. Over recent years, there has been a growing use of human medical imaging to assess pathologies, disease processes and drug action. These imaging modalities include PET, MRI, CT, ultrasound, EEG, SPECT and others (*British Medical Bulletin*, 2003, 65, 169-177). Therefore, the use of non-invasive imaging modalities, e.g. PET is an invaluable tool for the development of drugs in the future. Non-invasive nuclear imaging techniques can be used to obtain basic and diagnostic information about the physiology and biochemistry of a variety of living subjects. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. The use of radiotracers can result in images that contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject. Currently, radiotracers are available for obtaining useful information concerning cardiac function, myocardial blood flow, lung perfusion, liver function, brain blood flow, regional brain glucose and oxygen metabolism (WO2007/041025).

Furthermore,

PET imaging provides a non-invasive and quantitative assay of normal and abnormal neurochemistry in human at an early stage of the drug development to enhance the efficient and effective discovery of therapeutics.

Tracer doses of labeled compounds enable the early evaluation of novel drugs: bio-distribution studies; receptor occupancy studies to optimize drug-dosing regime and characterizing downstream responses of drug action.

Understanding disease mechanisms in human using non-invasive techniques is intimately connected with future developments in the diagnosis and management of diseases and of novel therapeutics.

Radionuclides commonly used in PET include $^{11}C$, $^{13}N$, $^{15}O$ or $^{18}F$. In principle, it is possible to label all drugs with each of these radionuclides, but only a few are found applicable as imaging agents in vivo in humans. The radioactive half-time of $^{11}C$, $^{13}N$, $^{15}O$ and $^{18}F$ are 20, 10, 2 and 110 min, respectively. These short half-lives provide a number of advantages as tracers to probe biological processes in vivo using PET. For example, repeat studies in the same subject can be made within the same day. PET increasingly is being used as a tool to determine drug-dose-enzyme/receptor occupancy relationships in well-defined compounds. The use of PET radiotracers that specifically bind to the target receptor or enzyme can provide information about the ability of a drug to enter the brain and bind to the target site, the degree of occupancy of the target site produced by a given dose of drug, the time-course of occupancy, and the relative plasma and tissue kinetics of the drug in question.

Occupancy studies are performed with PET radiotracers which are usually not identical to the drug candidate under study (*British Medical Bulletin*, 2003, 65, 169-177).

SUMMARY OF THE INVENTION

The present invention provides novel radiolabelled inhibitors of formula I for the Glycine 1 transporter (GlyT1), useful for the labelling and diagnostic imaging of the glycine 1 transporter functionality.

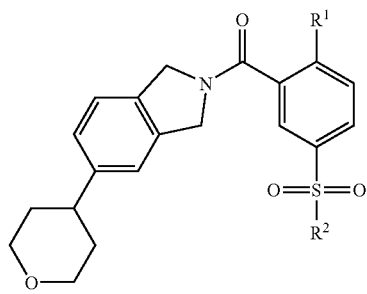

wherein

R¹ is isopropoxy or 2,2,2-trifluoro-1-methyl-ethoxy; and

R² is a radiolabelled group $CH_3$, wherein the radionuclide is $^3H$ or $^{11}C$.

The radiolabelled compounds of formula I can be used as PET (Positron Emission Tomography) radiotracers for the labelling and diagnostic molecular imaging of the glycine 1 transporter functionality. Radiolabelled compounds of formula I have potential to be used as imaging agents for visualizing the Glycine 1 transporter in humans. The present invention further provides the following radiolabelled compounds:

A Radiolabelled Compound of Formula I-A

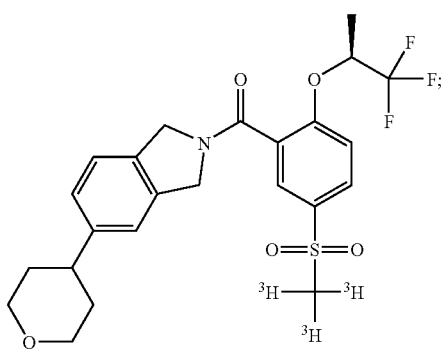

A Radiolabelled Compound of Formula I-B

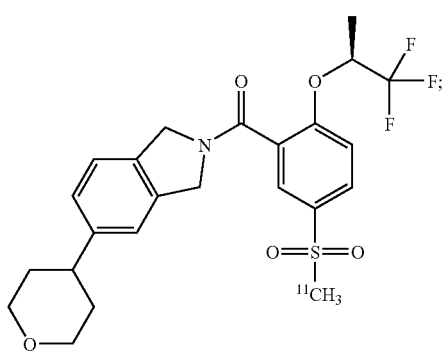

A Radiolabelled Compound of Formula I-C

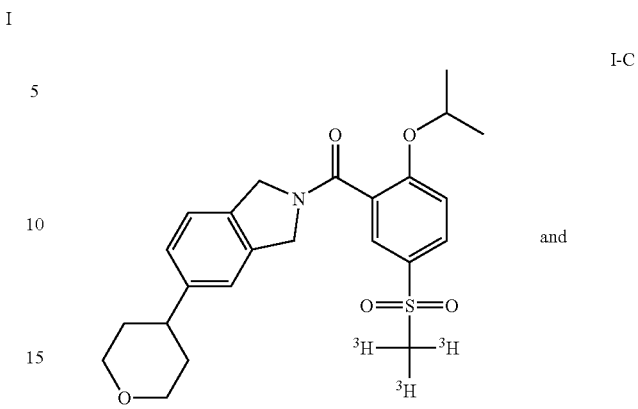

and

A Radiolabelled Compound of Formula I-D

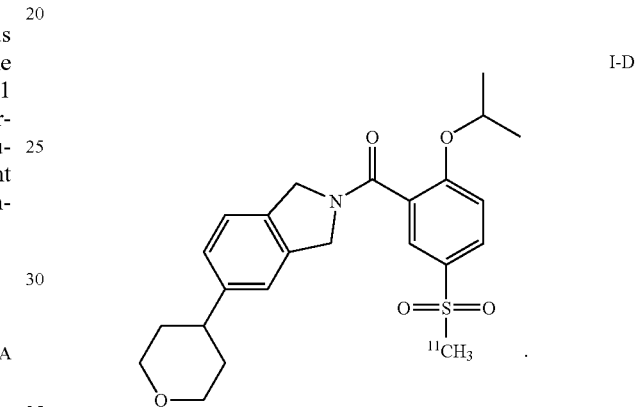

Further embodiments of the invention are the compounds of formula I for use as GlyT1 ligand, for use in a GlyT1 binding studies and for use as a PET radiotracers.

Furthermore the present compounds can be used for diagnostic imaging of GlyT1 in the brain of a mammal.

The invention comprises a method for the diagnostic imaging of the GlyT1 transporter which comprises administering to a mammal an effective amount of a compound of formula I and comprises a method for the detection of GlyT1 functionality in mammalian tissue which comprises administering to a mammal an effective amount of a compound of formula I. GlyT1 functionality means that GlyT1 is a selective transporter of glycine which is a neurotransmitter in the CNS.

The invention further provides a composition containing a compound of formula I and a pharmaceutically acceptable excipient for diagnostic imaging of GlyT1 in the brain of a mammal.

Glyt1 transporter inhibitors are useful for the treatment of illnesses, which are psychoses, pain, dysfunction in memory and learning, schizophrenia, dementia and other diseases in which cognitive processes are impaired, such as attention deficit disorders or Alzheimer's disease. The preferred indication is schizophrenia.

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments The non-radiolabelled compounds are known in the prior art and described in WO2006/082001 as GlyT1 transporter inhibitors.

Scheme 1 represents a synthetic route towards compounds of formula (I) wherein $R^2$ is a radiolabelled group:

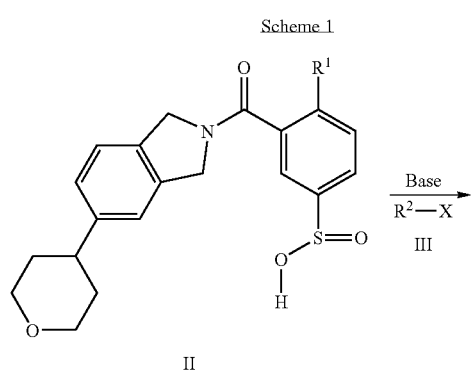

The compound of formula II is reacted with a base, such as cesium carbonate, and with a reagent of formula III, wherein $R^2$ is a group containing a radionuclide selected from $^3H$ or $^{11}C$, and X is a leaving group, such as iodine. Reagents of formula III like: [$^3H$]methyl iodide is known and [$^{11}C$]methyl iodide is known and prepared according to Larsen, P., Ulin, J., Dahlstrom, K. *J. Label. Compds. Radiopharm.* 37, 73-75, 1995.

Scheme 2 represents a synthetic route for the synthesis of a compound of formula (II) wherein $R^1$ is (S)-2,2,2-trifluoro-1-methyl-ethoxy.

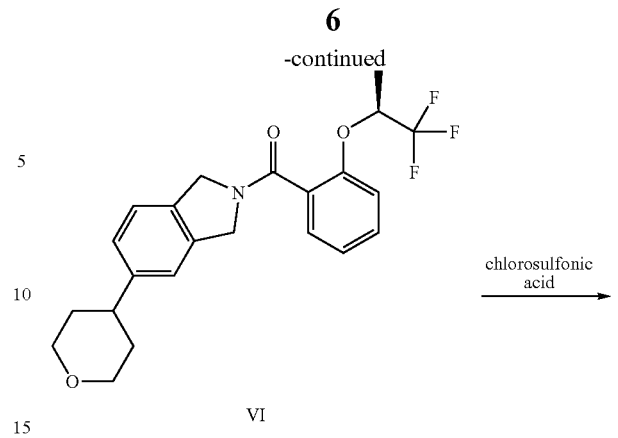

Intermediate acid IV can be prepared by reaction of commercially available ortho-fluoro benzoic acid with (S)-1,1,1-trifluoro-propan-2-ol (CAS: 3539-97-7) in the presence of a base, such as sodium hydride, in a solvent, such as dioxane. Coupling of acid IV with known isoindoline V (WO 2006082001) to yield the amide VI can be achieved in the presence of a coupling reagent, such as TBTU, and a base, such as diisopropylethylamine, in a solvent, such as DMF.

Chlorosulfonylation of VI to provide the sulfonyl chloride intermediate VII can be carried out in the presence of chlorosulfonic acid in a solvent, such as dichloroethane. Reduction of VII into sulfinic acid II can be achieved by using sodium sulfite as a reducing agent in a solvent like DMF and water.

Scheme 3 represents a synthetic route for the synthesis of compounds of formula (II) wherein $R^1$ is isopropoxy.

Scheme 3

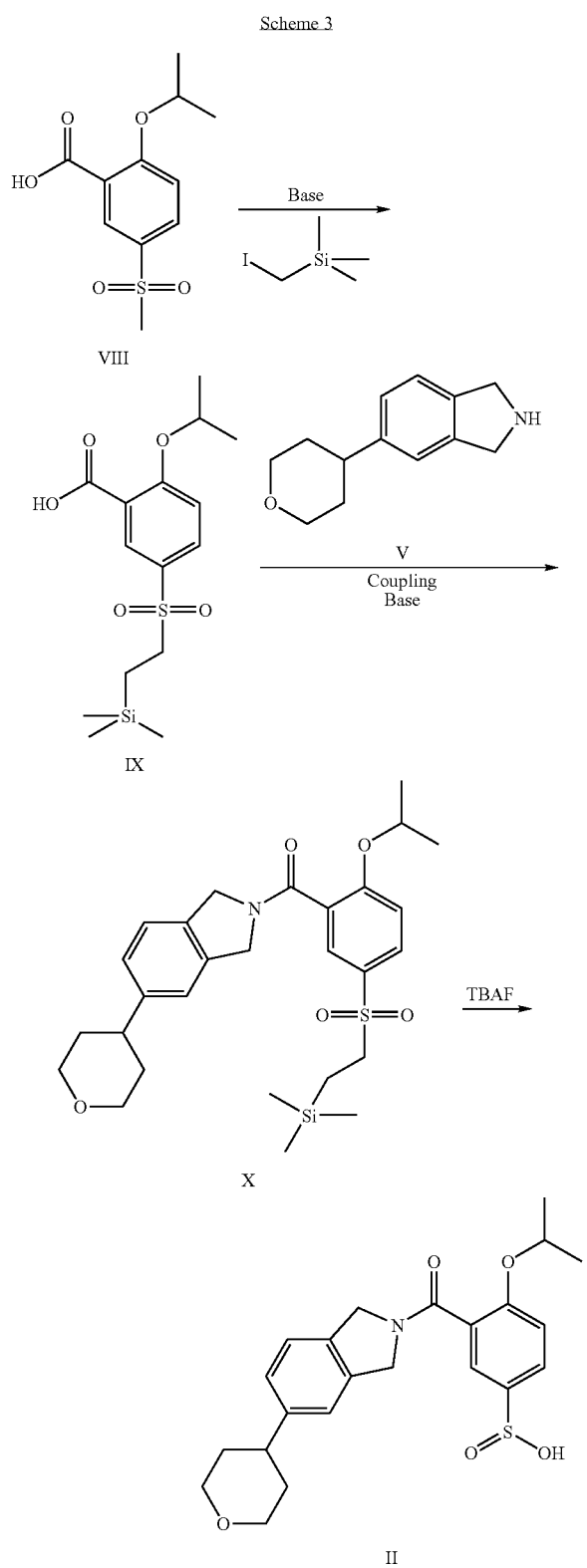

Intermediate IX can be prepared by reaction of acid VIII (WO 2005014563) with the commercially available alkylating agent (iodomethyl)trimethylsilane in the presence of a base, such as lithium diisopropylamide, and an additive, like TMEDA, in a solvent, such as THF. Coupling of acid IX with known isoindoline V (WO 2006082001) to yield the amide X can be achieved in the presence of a coupling reagent, such as TBTU, and a base, such as diisopropylethylamine, in a solvent, such as DMF. Transformation of X into sulfinic acid II can be achieved in the presence of TBAF in a solvent like THF.

ABBREVIATIONS

TBTU O-Benzotriazolyl tetramethylisouronium tetrafluoroborate
DMF Dimethylformamide
TBAF Tetrabutylammonium fluoride
THF Tetrahydrofuran
TMEDA Tetramethylethylenediamine
MTBE Methyl-tert-butyl ether
LDA Lithium diisopropylamide As described above, the radiolabelled compounds of formula I can be used as PET ligands for the labelling and diagnostic molecular imaging of the glycine 1 transporter functionality.

The corresponding unlabelled compounds [5-methanesulfonyl-2-((S)-2,2,2-trifluoro-1-methyl-ethoxy)-phenyl-5-(tetrahydro-pyran-4-yl)-1,3-dihydro-isoindol-2-yl]-methanone and (2-isopropoxy-5-methanesulfonyl-phenyl)-[5-(tetrahydro-pyran-4-yl)-1,3-dihydro-isoindol-2-yl]-methanone] are active on the GlyT1 transporter in vitro with a $IC_{50}$ value (µM) of 0.028 and 0.014, respectively. The test method is described in WO2006/082001.

Autoradiographic Studies in Rat Brain

The distribution of the binding sites of [$^3$H][5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone and [$^3$H][2-Isopropoxy-5-methanesulfonyl-phenyl)-[5-(tetrahydro-pyran-4-yl)-1,3-dihydro-isoindol-2-yl]-methanone] was investigated in the rat brain.

Male Wistar rats were used for these experiments. Rats were sacrificed; their brains were rapidly removed, frozen in dry ice powder. Ten µm-thick sagittal sections were cut in a Cryostat and thaw-mounted on adhesion glass slides. Brain sections were first incubated for 10 min. in Ringer buffer (NaCl 120 mM, KCl 5 mM, $CaCl_2$ 2 mM, $MgCl_2$ 1 mM, Tris-HCl 50 mM pH 7.4) at 37° C. and then for 60 min. in Ringer buffer at 37° C. containing either [$^3$H]5-Methanesulfonyl-2-((S)-2,2,2-trifluoro-1-methyl-ethoxy)-phenyl]-[5-(tetrahydro-pyran-4-yl)-1,3-dihydro-isoindol-2-yl-methanone or [$^3$H]-[2-Isopropoxy-5-methanesulfonyl-phenyl)-[5-(tetrahydro-pyran-4-yl)-1,3-dihydro-isoindol-2-yl]-methanone] at concentration 1 nM. For the evaluation of the non-specific-binding (NSB) of the radiotracer an additional group of sections was incubated with Ringer buffer containing the radiotracer and the reference GlyT1 inhibitor Org 24598 at the concentration 10 µM (60 in at 37° C.). At the end of the incubation, sections were rinsed 2×5 min. and 1×15 min. in ice-cold (4° C.) Ringer buffer and then rapidly dipped three times in distilled water at 4° C. Slide-mounted brain sections were dried under a flow of cold air and exposed together with [$^3$H]-microscale to a Fuji Imaging plate for 5 days. The imaging plate was then scanned in a FujiFilm high resolution plate scanner. The total amount of radiotracer bound to the brain areas of interest (TB) were measured using the MCID image analysis program and expressed as fmol of bound radiotracer/mg of protein. The amount of [$^3$H]5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone specifically bound to the GlyT1 carrier (SB) was calculated according to the formula: SB=TB−NSB.

The results obtained showed that the distribution of the binding sites of [³H]5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone and [³H][2-Isopropoxy-5-methanesulfonyl-phenyl)-[5-(tetrahydro-pyran-4-yl)-1,3-dihydro-isoindol-2-yl]-methanone] corresponded to the known distribution of the GlyT1 transporter [Cubelos B., Gimenez C., Zafra F., Cereb Cortex 15, 448-459, 2005; Zafra F., Aragon C., Olivares L., Danbolt N C, Gimenez C., Storm-Mathisen J., J Neuroscience. 15, 3952-69, 1995]. High densities of binding sites were observed in the thalamus, the brainstem, pons and medulla oblungata and the cerebellum. Lower densities were observed in the striatum, cortex and hippocampus. Co-incubation of the radiotracers with high concentrations of the specific GlyT1 inhibitor Org 24598 or other specific Glyt1 inhibitors completely abolished binding of both [³H]5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone and [³H][2-Isopropoxy-5-methanesulfonyl-phenyl)-[5-(tetrahydro-pyran-4-yl)-1,3-dihydro-isoindol-2-yl]-methanone] to rat brain sections confirming that both radiotracers bind to the GlyT1 transporter.

In Vivo PET Studies in the Baboon

1) PET imaging with [¹¹C-][2-Isopropoxy-5-methanesulfonyl-phenyl)-[5-(tetrahydro-pyran-4-yl)-1,3-dihydro-isoindol-2-yl]-methanone] and [¹¹C]-5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone The experiments described below were carried out in male baboons (papio anubis). Animals were fasted for 12 hours prior to the PET study. Baboons were initially sedated intramuscularly with Ketamine hydrochloride with restraint dosages of 5-7 mg/kg to achieve a light plane of anesthesia and then maintained on continuous Propofol intravenous infusion @ 0.3-0.4 mg/kg/h (DIPRIVAN® Injectable Emulsion). Circulatory volume was maintained by infusion of isotonic saline. A femoral arterial catheter was inserted for blood sampling. Physiological vital signs including heart rate, ECG, blood pressure (Spacelabs Monitor, Issaquah, Wash., USA) and oxygen saturation (Nellcor OxiMax® N-600™ Pulse Oximeter, Pleasanton, Calif., USA) were continuously monitored throughout the study. The animal was positioned in an ECAT HRRT® brain PET scanner (High Resolution Research Tomograph, CPS Innovations, Inc., Knoxville, Tenn.). The head of the animal was fitted with a thermoplastic mask that was attached to a head holder for reproducible fixation. A 6 min transmission scan with a 1 mCi Cs-137 point source was initially done for attenuation correction. [¹¹C-][2-Isopropoxy-5-methanesulfonyl-phenyl)-[5-(tetrahydro-pyran-4-yl)-1,3-dihydro-isoindol-2-yl]-methanone] and [¹¹C]-5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone were administered intravenously as a 1 minute bolus injection. PET scanning and arterial blood sampling was initiated upon start of the radiotracer administration and PET images were acquired from 0 to 90 minutes following administration of the radiotracer.

The results of these imaging studies showed that both radiotracers [¹¹C][2-Isopropoxy-5-methanesulfonyl-phenyl)-[5-(tetrahydro-pyran-4-yl)-1,3-dihydro-isoindol-2-yl]-methanone] and [¹¹C]-5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone) were rapidly taken up in multiple brain areas with time activity curves that demonstrated peak uptake 20-30 min after administration and a slow decline over the remainder of the study. The regional distribution of both radiotracers reflected the known distribution of the glycine transporter 1 (GlyT1) with higher accumulation in the pons, brainstem, cerebellum, and thalamus compared to cortical regions (Cubelos B., Gimenez C., Zafra F., Cereb Cortex 15, 448-459, 2005).

2) PET Imaging with Pharmacological Challenges

These experiments tested the ability of unlabeled GlyT1 inhibitors to block the uptake of [¹¹C][2-Isopropoxy-5-methanesulfonyl-phenyl)-[5-(tetrahydro-pyran-4-yl)-1,3-dihydro-isoindol-2-yl]-methanone] and [¹¹C]-5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone in brain regions known to contain GlyT1. Since both of [5-methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone and (2-isopropoxy-5-methanesulfonyl-phenyl)-[5-(tetrahydro-pyran-4-yl)-1,3-dihydro-isoindol-2-yl]-methanone are selective GlyT1 inhibitors, one of these compounds, [5-methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone, was selected for the experiments described below.

Each animal received two sequential administrations of the radiotracer on the same day. The first administration of radiotracer was used to determine radiotracer baseline uptake. Following the baseline scan, the baboon received an intravenous administration of unlabeled [5-methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone (blocker). The blocker infusion started 20 min before (the second) radiotracer injection. The blocker was first infused at dose=0.2 mg/kg. After 10 min, the flow rate was changed to deliver 0.5 mg/kg for the remainder 100 min of the study.

Preliminary pharmacokinetic experiments and modeling of the data indicated that these rates of infusion produce constant plasma levels of [5-methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone during the PET scan time interval.

Pretreatment with cold [5-methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone (a selective GlyT1 inhibitor) completely blocked the specific uptake of both radiotracers [¹¹C-][2-Isopropoxy-5-methanesulfonyl-phenyl)-[5-(tetrahydro-pyran-4-yl)-1,3-dihydro-isoindol-2-yl]-methanone] and [¹¹C]-5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone) and led to a homogenous distribution of radioactivity throughout the brain. These results confirmed the specificity of both radiotracers for the GlyT1 transporter and clearly showed that their binding to the GlyT-1 transporter can be reduced by unlabeled drugs that bind to the GlyT1 transporter.

The compounds of the present invention are diagnostic tools which can be helpful in the diagnosis of disorders of the central nervous system, for example for schizophrenia, cognitive impairment and Alzheimer's disease.

The compounds of formula I can be processed with pharmaceutically inert inorganic or organic carriers for the production of pharmaceutical compositions.

The dosage at which compounds of the invention can be administered can vary within wide limits and will, of course, have to be adjusted to the individual requirements in each particular case.

The radiolabelled inhibitors are preferably administered intravenously.

An injection solution can have the following composition:

| | |
|---|---|
| Compound of formula (I) | 1 mg |
| 1 n HCl | 20 µl |
| acetic acid | 0.5 mg |
| NaCl | 8 mg |
| phenol | 10 mg |
| 1 n NaOH | q.s. ad pH 5 |
| H₂O | q.s. ad 1 ml |

The following examples illustrate the invention but are not intended to limit its scope.

EXAMPLE 1

[3H-methyl]-[5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone

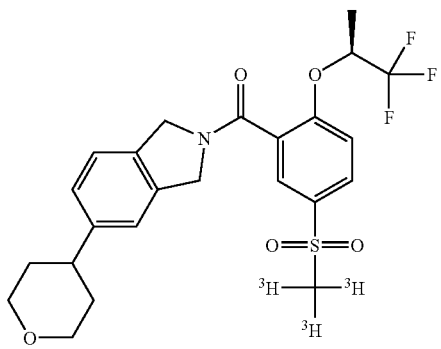

a) Step 1

2-((S)-2,2,2-Trifluoro-1-methyl-ethoxy)-benzoic acid

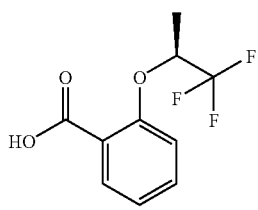

36.0 g (316 mmol) of (S)-1,1,1-trifluoro-propan-2-ol (CAS: 3539-97-7) was added to a cold (0 to 5° C.) suspension of 17.0 g (425 mmol) of NaH (pract., 60%) in 200 ml of dioxane. The suspension was stirred at room temperature during 0.5 h then cooled (0 to 5° C.) and a solution of 20.0 g (143 mmol) of 2-fluoro-benzoic acid in 100 ml of dioxane was added. The mixture was stirred during 0.5 h at room temperature and during 140 h under reflux. The mixture was poured into 800 ml of water, washed with 300 ml of MTBE, then acidified to pH 2 with hydrochloric acid and the product was extracted with MTBE. The solvent was concentrated in vacuo and the residue was crystallized from ethanol/water to provide 27.3 g (82%) of the title compound as a white solid. MS (m/e): 234.1 [M]⁺.

b) Step 2

[5-(Tetrahydro-pyran-4-yl)-1,3-dihydro-isoindol-2-yl]-[2-((S)-2,2,2-trifluoro-1-methyl-ethoxy)-phenyl]-methanone

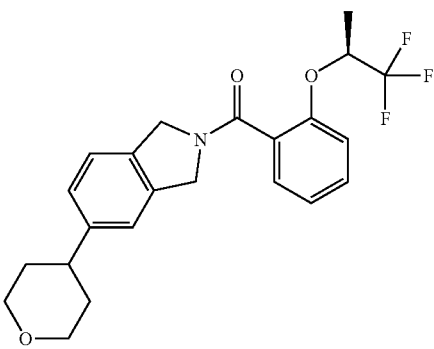

To a solution of 0.9 g (3.8 mmol) 2-((S)-2,2,2-trifluoro-1-methyl-ethoxy)-benzoic acid in 9 ml DMF under argon at room temperature, was added 1.4 g (4.2 mmol) TBTU, 3.3 ml (19.2 mmol) N-ethyldiisopropylamine and finally 0.8 g (3.8 mmol) 5-(tetrahydro-pyran-4-yl)-2,3-dihydro-1H-isoindole (CAS: 905274-50-2). The mixture was stirred at room temperature overnight. The solvent was removed in vacuo. The residue was dissolved in ethyl acetate. The solution was washed twice with water and twice with sat. NaHCO₃ solution, dried over Na₂SO₄, filtered and concentrated in vacuo. The crude oil was purified with flash column chromatography on silica eluting with a gradient formed from heptane and ethylacetate to provide 1.5 g (93%) of the title compound as a yellow oil. MS (m/e): 420.2 [M+H]⁺.

c) Step 3

3-[5-(Tetrahydro-pyran-4-yl)-1,3-dihydro-isoindole-2-carbonyl]-4-((S)-2,2,2-trifluoro-1-methyl-ethoxy)-benzenesulfonyl chloride

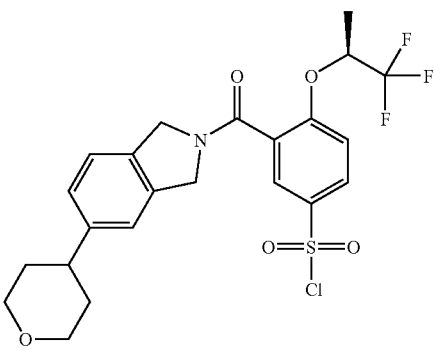

A solution of 0.2 g (0.47 mmol) [5-(tetrahydro-pyran-4-yl)-1,3-dihydro-isoindol-2-yl]-[2-((S)-2,2,2-trifluoro-1-methyl-ethoxy)-phenyl]-methanone in 2 ml of 1,2-dichloroethane was added dropwise to 0.32 ml (4.7 mmol) chlorosulfonic acid under ice bath cooling. The mixture was stirred at room temperature for 30 minutes and then at 55° C. for 30 minutes. The mixture was cooled in an ice bath and quenched by dropwise addition of 2 ml water. The mixture was diluted with dichloromethane. The organic layer was separated and the aqueous layer was extracted twice with dichloromethane. The combined dichloromethane extracts were dried over $Na_2SO_4$, filtered and concentrated in vacuo. The obtained foam was stirred with ethylacetate. The solid was filtrated. The filtrate was washed twice with a saturated solution of $NaHCO_3$, dried over $Na_2SO_4$, filtered and concentrated in vacuo to provide 0.12 g (51%) of the title compound as light yellow foam. MS (m/e): 517.1 $[M]^+$.

d) Step 4

3-[5-(Tetrahydro-pyran-4-yl)-1,3-dihydro-isoindole-2-carbonyl]-4-((S)-2,2,2-trifluoro-1-methyl-ethoxy)-benzenesulfinate sodium salt

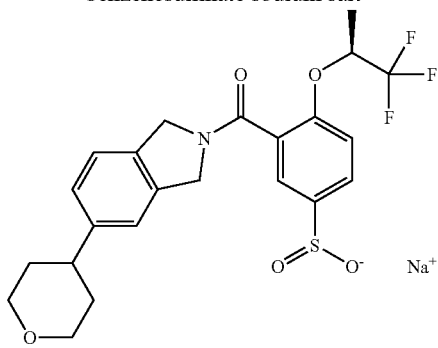

1.15 g (8.94 mmol) of $Na_2SO_3$ and 1.70 g (9.60 mmol) of $Na_2HPO_4$ hydrate were dissolved in 13 ml water. An ethanolic solution of 2.40 g (4.63 mmol) of 3-[5-(tetrahydro-pyran-4-yl)-1,3-dihydro-isoindole-2-carbonyl]-4-((S)-2,2,2-trifluoro-1-methyl-ethoxy)-benzenesulfonyl chloride was added. The reaction mixture was stirred at 35 to 40° C. during 1 hour and then overnight at room temperature. 1.3 g Speedex was added, the reaction mixture was filtered and the filtrate was evaporated. The crude product was treated with aqueous citric acid/NaCl solution then extracted with MTBE/THF 1:1. The organic solvent was evaporated and the residue was dissolved in MeOH/water (2:1), and treated with 800 mg (9.52 mmol) of $NaHCO_3$. 1 g Speedex was added and the reaction mixture was filtrated and concentrated in vacuo. The residue was purified chromatographically by using a reverse phase column (RP-18, water/methanol) to provide 1.12 g (48%) of the title compound as a white foam. MS (m/e): 484.3 $[M+H]^+$.

e) Step 5

[³H-methyl]-[5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone

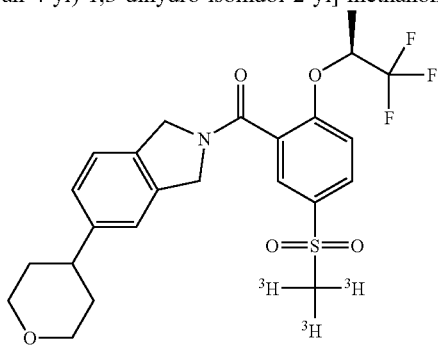

0.16 mg (1.2 μmol) of LiI were added to a solution of 50 mCi (0.15 mg, 0.6 μmol) of [³H]methyl nosylate in 0.2 ml of DMF. After stirring of the reaction mixture for 3 h at 20° C. in a closed vial, 0.6 mg (1.4 mol) of 3-[5-(tetrahydro-pyran-4-yl)-1,3-dihydro-isoindole-2-carbonyl]-4-((S)-2,2,2-trifluoro-1-methyl-ethoxy)-benzenesulfinate sodium salt and 1.0 mg (3.1 μmol) of cesium carbonate were added and stirring was continued for 2 h at 20° C. The reaction mixture was treated with water and brine and was then extracted with ethyl acetate. After evaporation of the organic solvent the resulting crude product was purified by column chromatography (silica, ethyl acetate/heptane 4:1) to yield 23.9 mCi (48%) of the tritiated title compound in a specific activity of 74 Ci/mmol (according to MS analysis). Radio-HPLC analysis indicated a radiochemical purity of >99%.

EXAMPLE 2

[¹¹C-methyl]-[5-Methanesulfonyl-2-((S)-2,2,2-trifluoro-1-methyl-ethoxy)-phenyl]-[5-(tetrahydro-pyran-4-yl)-1,3-dihydro-isoindol-2-yl]-methanone

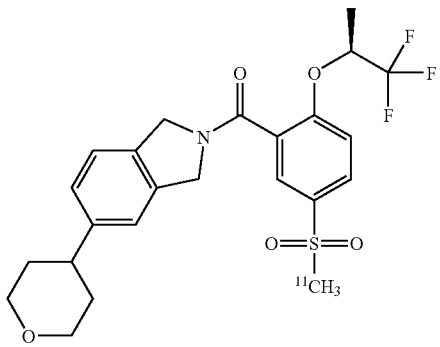

3-[5-(Tetrahydro-pyran-4-yl)-1,3-dihydro-isoindole-2-carbonyl]-4-((S)-2,2,2-trifluoro-1-methyl-ethoxy)-benzenesulfinate sodium salt (1 mg, 2 μmole) was dissolved in 100 μL of dimethylformamide. The vial was sealed; the solution was shaken for one minute and was injected into the Bioscan AutoLoop System and flushed with argon (30 mL/min) for 5 seconds. [¹¹C]Methyl iodide (prepared according to Larsen, P., Ulin, J., Dahlstrom, K. *J. Label. Compds. Radiopharm.* 37, 73-75, 1995) was transferred into the Bioscan Autoloop (Bioscan Inc, Washington, D.C.) in a stream of helium (30 mL/min). The [¹¹C]methyl iodide was trapped in the AutoLoop for 3.5 minutes before the flow was stopped. After 4.5 minutes, the reaction mixture was automatically transferred to a semipreparative HPLC and worked up as follows. The product was collected in a pressure reservoir where it was diluted with 50 ml of water, then loaded onto a Waters C-18 SepPak Plus (see analytical and preparative HPLC conditions below). The SepPak containing the purified title compound was washed with 10 ml of normal saline before the product was eluted with 1 ml of absolute ethanol followed by 10 ml of normal saline through a 0.22 micron filter for sterilization into a sterile, pyrogen-free vial containing 4 mL of normal saline. HPLC Conditions:Analytical: Onyx $C_{18}$ 4.6×100 mm 35:65 MeCN:$H_2O$ TEA pH 7.2 at 3 mL/min Prep: XTerra $C_{18}$ 5μ 19×100 mm 40:60 MeCN:$H_2O$ 0.1 M $NH_4$ formate at 18 mL/min.

EXAMPLE 3

[³H-methyl]-(2-Isopropoxy-5-methanesulfonyl-phenyl)-[5-(tetrahydro-pyran-4-yl)-1,3-dihydro-isoindol-2-yl]-methanone

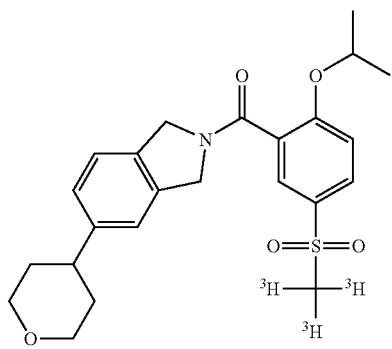

a) Step 1

2-Isopropoxy-5-(2-trimethylsilanyl-ethanesulfonyl)-benzoic acid

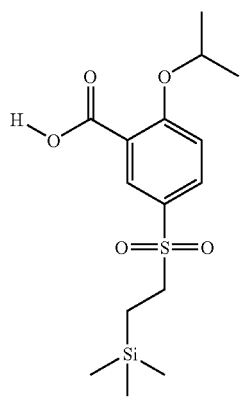

To a stirred −70° C. suspension of 0.26 g (1 mmol) 2-isopropoxy-5-methanesulfonyl-benzoic acid (CAS: 845616-02-6) and 0.75 ml (5 mmol) TMEDA in 2.6 ml THF was added dropwise a LDA solution (prepared from a 1.3 ml (2.1 mmol) 1.6M n-butyllithium solution in hexane and 0.3 ml (2.1 mmol) diisopropylamine in 2.5 ml THF at 0° C.). The light yellow suspension was stirred at −70° C. for 30 minutes. A solution of 0.19 ml (1.3 mmol) (iodomethyl)trimethylsilane in 0.5 ml THF was added dropwise over a period of 5 minutes. The yellow suspension was stirred at −70° C. for 15 minutes and then allowed to warm to room temperature. The light yellow solution was stirred at room temperature for 1 hour and then quenched with 5 ml brine. The mixture was diluted with 5 ml water. The mixture was concentrated in vacuo. The aqueous layer was carefully acidified with HCl 1N and extracted 3 times with dichloromethane. The combined extracts were dried over $Na_2SO_4$, filtered and concentrated in vacuo. The crude was purified with flash column chromatography on silica eluting with a gradient formed from heptane and ethylacetate to provide 0.21 g (63%) of the title compound as a yellow oil. MS (m/e): 343.0 [M−H]⁺.

b) Step 2

[2-Isopropoxy-5-(2-trimethylsilanyl-ethanesulfonyl)-phenyl]-[5-(tetrahydro-pyran-4-yl)-1,3-dihydro-isoindol-2-yl]-methanone

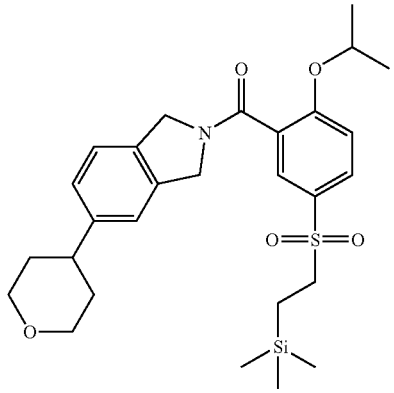

In analogy to the procedure described for the synthesis of example 1, step 2, the title compound was prepared from 5-(tetrahydro-pyran-4-yl)-2,3-dihydro-1H-isoindole (CAS: 905274-50-2) and 2-isopropoxy-5-(2-trimethylsilanyl-ethanesulfonyl)-benzoic acid. MS (m/e): 529.3 [M]⁺.

c) Step 3

4-Isopropoxy-3-[5-(tetrahydro-pyran-4-yl)-1,3-dihydro-isoindole-2-carbonyl]-benzene sulfinate sodium salt

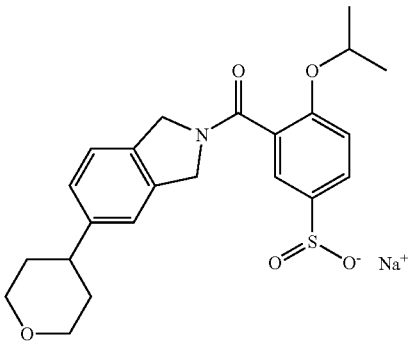

1.40 g (2.64 mmol) of [2-isopropoxy-5-(2-trimethylsilanyl-ethanesulfonyl)-phenyl]-[5-(tetrahydro-pyran-4-yl)-1,3-dihydro-isoindol-2-yl]-methanone was dissolved in 14 ml of THF and treated with 4.0 ml (4.0 mmol) of a 1 M solution of TBAF in THF at 60° C. during 3.5 hours. The reaction mixture was poured on an aqueous solution of citric acid/NaCl, then extracted with MTBE/THF 1:1. The organic solvent was evaporated, the residue was dissolved in MeOH/water (3:1) and treated with 600 mg of $NaHCO_3$. After evaporation, the residue was purified chromatographically on a reverse phase column (RP-18, water/methanol) to provide 0.66 g (55%) of the title compound as a white foam. MS (m/e): 430.2 [M+H]⁺.

d) Step 4

[³H-methyl]-(2-Isopropoxy-5-methanesulfonyl-phenyl)-[5-(tetrahydro-pyran-4-yl)-1,3-dihydro-isoindol-2-yl]-methanone

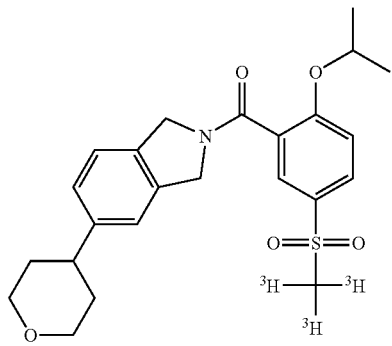

0.16 mg (1.2 µmol) of LiI were added to a solution of 50 mCi (0.15 mg, 0.6 µmol) of [³H]methyl nosylate in 0.2 ml of DMF. After stirring of the reaction mixture for 3 h at 20° C. in a closed vial 0.6 mg (1.3 µmol) of 4-isopropoxy-3-[5-(tetrahydro-pyran-4-yl)-1,3-dihydro-isoindole-2-carbonyl]-benzene sulfinate sodium salt and 1.0 mg (3.1 µmol) of cesium carbonate were added and stirring was continued for 2 h at 20° C. The reaction mixture was treated with water and brine and was then extracted with ethyl acetate. After evaporation of the organic solvent the resulting crude product was purified by column chromatography (silica, ethyl acetate/heptane 4:1) to yield 29.2 mCi (59%) of the tritiated title compound in a specific activity of 74 Ci/mmol (according to MS analysis). Radio-HPLC analysis indicated a radiochemical purity of >99%.

EXAMPLE 4

[¹¹C-methyl]-(2-Isopropoxy-5-methanesulfonyl-phenyl)-[5-(tetrahydro-pyran-4-yl)-1,3-dihydro-isoindol-2-yl]-methanone

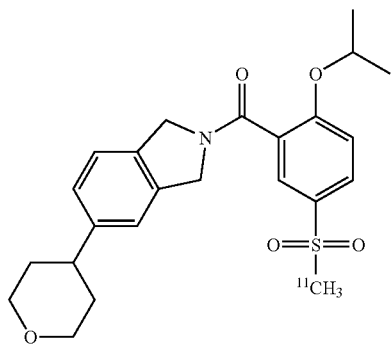

In analogy to the procedure described for the synthesis of example 2, the title compound was prepared from 4-isopropoxy-3-[5-(tetrahydro-pyran-4-yl)-1,3-dihydro-isoindole-2-carbonyl]-benzene sulfinate sodium salt and [¹¹C]methyl iodide.

The invention claimed is:

1. A radiolabelled compound of formula I

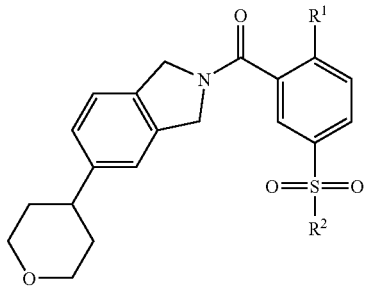

wherein
R¹ is isopropoxy or 2,2,2-trifluoro-1-methyl-ethoxy; and
R² is a radiolabelled group CH₃, wherein the radionuclide is ³H or ¹¹C.

2. The radiolabelled compound of claim 1, having formula I-A

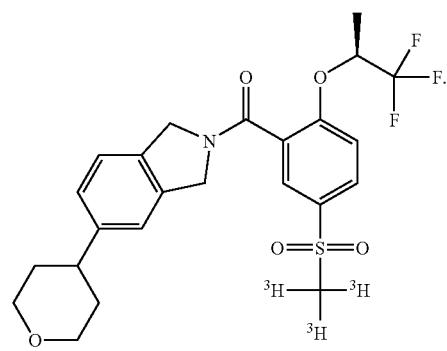

3. The radiolabelled compound of claim 1, having formula I-B

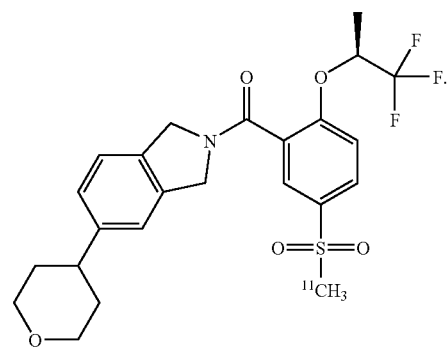

4. The radiolabelled compound of claim 1, having formula I-C

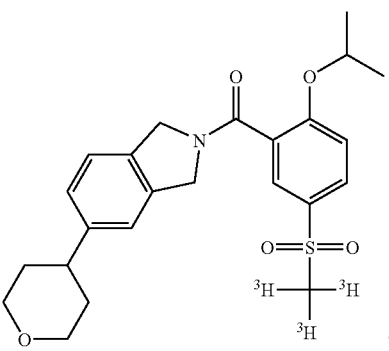

5. The radiolabelled compound of claim 1, having formula I-D

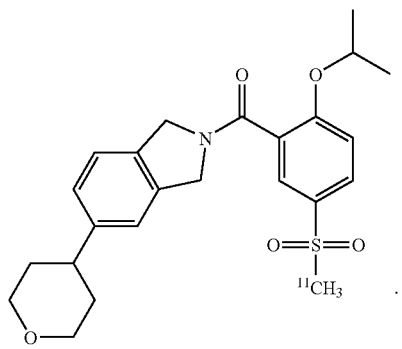

6. A pharmaceutical composition comprising a compound of formula I

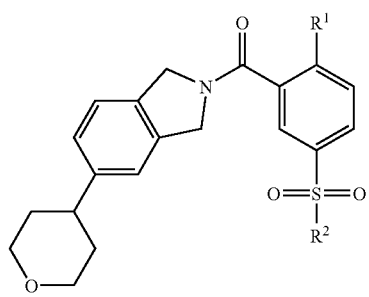

wherein
R¹ is isopropoxy or 2,2,2-trifluoro-1-methyl-ethoxy; and
R² is a radiolabelled group CH₃, wherein the radionuclide is ³H or ¹¹C and a pharmaceutically acceptable excipient.

7. The pharmaceutical composition of claim 6, wherein the compound of formula I is a compound of formula I-A

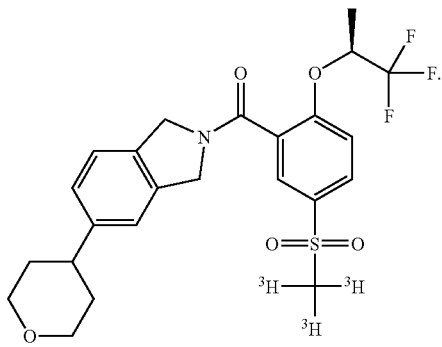

8. The pharmaceutical composition of claim 6, wherein the compound of formula I is a compound of formula I-B

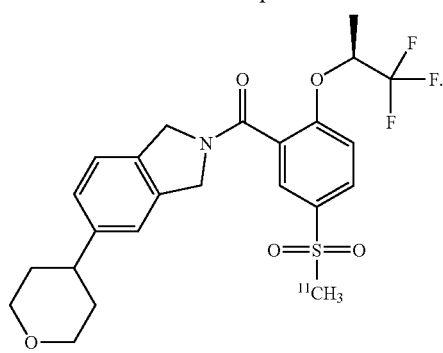

9. The pharmaceutical composition of claim 6, wherein the compound of formula I is a compound of formula I-C

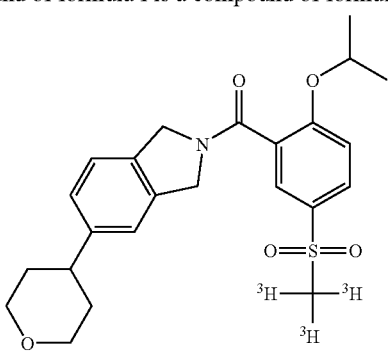

10. The pharmaceutical composition of claim 6, wherein the compound of formula I is a compound of formula I-D

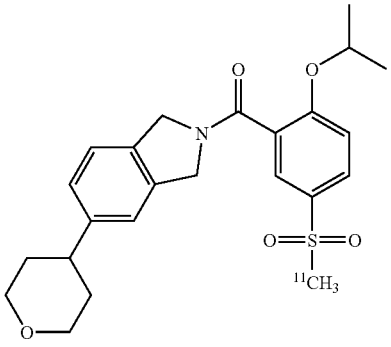

* * * * *